(12) United States Patent
Mansour et al.

(10) Patent No.: US 9,375,561 B2
(45) Date of Patent: Jun. 28, 2016

(54) SELF-FLUSHING VALVE

(75) Inventors: George Mansour, Pomona, CA (US); Chris Zollinger, Chino Hills, CA (US)

(73) Assignee: CareFusion 303, Inc., San Diego, CA (US)

( * ) Notice: Subject to any disclaimer, the term of this patent is extended or adjusted under 35 U.S.C. 154(b) by 314 days.

(21) Appl. No.: 13/225,015

(22) Filed: Sep. 2, 2011

(65) Prior Publication Data

US 2013/0060205 A1 Mar. 7, 2013

(51) Int. Cl.
*A61M 39/22* (2006.01)
*A61M 39/26* (2006.01)
*A61M 39/24* (2006.01)

(52) U.S. Cl.
CPC .............. *A61M 39/223* (2013.01); *A61M 39/26* (2013.01); *A61M 2039/2426* (2013.01)

(58) Field of Classification Search
CPC ...................... A61M 2039/229; A61M 39/045; A61M 39/223; F16K 11/0833; F16K 11/0853; F16K 27/065; F16K 5/0407
USPC ................ 604/256, 83, 32, 167.05, 181–183; 137/556.6, 903
See application file for complete search history.

(56) References Cited

U.S. PATENT DOCUMENTS

| | | | | |
|---|---|---|---|---|
| 3,610,228 A * | 10/1971 | Temkin | ............... | A61B 5/02156 600/486 |
| 3,721,265 A * | 3/1973 | Hoffland | ................. | F16K 11/08 137/625.47 |
| 3,774,604 A * | 11/1973 | Danielsson | ............... | 604/167.05 |
| 3,834,372 A * | 9/1974 | Turney | ................. | A61B 5/0215 137/625.47 |
| 3,952,729 A * | 4/1976 | Libman et al. | ................. | 600/575 |
| 4,219,021 A * | 8/1980 | Fink | ............................ | 137/556.6 |
| 4,252,122 A * | 2/1981 | Halvorsen | ....................... | 604/83 |
| 4,447,235 A * | 5/1984 | Clarke | ............... | A61B 17/3415 600/573 |
| 4,915,687 A * | 4/1990 | Sivert | ............................. | 604/83 |
| 4,967,797 A * | 11/1990 | Manska | ............. | A61M 39/223 137/625.47 |
| 4,981,140 A * | 1/1991 | Wyatt | ................... | A61B 5/1405 600/486 |
| 5,046,528 A * | 9/1991 | Manska | ........................ | 137/556 |
| 5,340,364 A * | 8/1994 | Ghelli | .................. | A61B 5/1427 604/30 |
| 5,466,228 A * | 11/1995 | Evans | .................. | F16K 11/0853 137/625.47 |
| 5,533,549 A * | 7/1996 | Sherman | ....................... | 137/557 |
| 5,540,668 A * | 7/1996 | Wilson et al. | ................. | 604/248 |
| 5,605,630 A * | 2/1997 | Shibata | ......................... | 210/646 |

(Continued)

FOREIGN PATENT DOCUMENTS

EP 1593405 A1 11/2005
EP 1857136 A1 11/2007

(Continued)

OTHER PUBLICATIONS

International Search Report and Written Opinion for PCT/US2012/051007, mailed Feb. 14, 2013.

(Continued)

*Primary Examiner* — Kami A Bosworth
*Assistant Examiner* — Matthew A Engel
(74) *Attorney, Agent, or Firm* — McDermott Will & Emery LLP

(57) ABSTRACT

A valve is disclosed that has a body with an inlet, an outlet, and a needleless access port coupled to the body. The access port has an interior space and is configured to be actuated by a needleless connector. The inlet is selectively coupled to the outlet through the interior space such that fluid entering the inlet entirely flows through the interior space to the outlet.

15 Claims, 7 Drawing Sheets

(56) References Cited

U.S. PATENT DOCUMENTS

| | | | |
|---|---|---|---|
| 5,782,816 A * | 7/1998 | Werschmidt et al. | 604/256 |
| 6,177,049 B1 * | 1/2001 | Schnell et al. | 422/44 |
| 6,418,966 B2 * | 7/2002 | Loo | 137/625.47 |
| 6,439,262 B1 * | 8/2002 | Hosono et al. | 137/505.41 |
| 6,457,488 B2 * | 10/2002 | Loo | 137/625.47 |
| 6,855,138 B2 * | 2/2005 | Tsai | A61M 39/26 604/537 |
| 7,081,109 B2 * | 7/2006 | Tighe | A61M 39/20 604/500 |
| 7,172,572 B2 * | 2/2007 | Diamond | A61M 39/223 137/625.21 |
| 7,510,545 B2 * | 3/2009 | Peppel | A61M 39/045 604/256 |
| 7,744,573 B2 * | 6/2010 | Gordon | A61B 5/1427 600/584 |
| 7,771,383 B2 * | 8/2010 | Truitt | A61M 39/02 604/246 |
| 7,875,020 B2 * | 1/2011 | Tighe | A61M 39/20 604/539 |
| 7,963,951 B2 * | 6/2011 | Kitani et al. | 604/248 |
| 7,984,730 B2 * | 7/2011 | Ziv | A61M 39/223 137/239 |
| 7,988,128 B2 * | 8/2011 | Wentling | 251/286 |
| 7,993,328 B2 * | 8/2011 | Whitley | 604/537 |
| 8,002,727 B2 * | 8/2011 | Brugger et al. | 604/6.1 |
| 8,221,389 B2 * | 7/2012 | Brenner et al. | 604/537 |
| 8,298,196 B1 * | 10/2012 | Mansour | 604/256 |
| 8,534,321 B2 * | 9/2013 | Ziv | A61M 39/223 137/239 |
| 8,584,701 B2 * | 11/2013 | Duncan | F16K 11/0853 116/277 |
| 8,715,222 B2 * | 5/2014 | Truitt | A61M 39/02 604/246 |
| 9,016,316 B2 * | 4/2015 | Ziv | A61M 39/223 137/239 |
| 2004/0210162 A1 * | 10/2004 | Wyatt | A61B 5/1405 600/573 |
| 2006/0027270 A1 * | 2/2006 | Truitt et al. | 137/843 |
| 2006/0089603 A1 | 4/2006 | Truitt et al. | |
| 2007/0219483 A1 * | 9/2007 | Kitani et al. | 604/32 |
| 2007/0287953 A1 * | 12/2007 | Ziv et al. | 604/31 |
| 2010/0004634 A1 * | 1/2010 | Whitley | 604/537 |
| 2010/0063440 A1 * | 3/2010 | Kitani et al. | 604/83 |
| 2012/0316514 A1 * | 12/2012 | Mansour | 604/256 |

FOREIGN PATENT DOCUMENTS

| | | |
|---|---|---|
| WO | WO-2008091698 A2 | 7/2008 |
| WO | WO-2010073643 A1 | 7/2010 |
| WO | WO-2010120051 A2 | 10/2010 |
| WO | WO-2011060384 A1 | 5/2011 |

OTHER PUBLICATIONS

International Preliminary Report on Patentability for International Application No. PCT/US2012/051007, dated Mar. 4, 2014, 8 pages.
Extended European Search Report for European Application No. 12828019, dated Feb. 23, 2015, 7 pages.

\* cited by examiner

SELF-FLUSHING VALVE

BACKGROUND

1. Field

The present disclosure is related to fluid valves and, in particular, to intravenous (IV) administration of medical fluids using IV sets with valves having an access port.

2. Description of the Related Art

Patients in hospitals are often provided with medical fluids that are administered through an IV infusion. The medical fluids may include a saline solution to hydrate the patient or a more complex mixture, such as Ringer's Lactate, that may include electrolytes or nutritional supplements. It is sometimes desirable to intravenously administer a small amount of a second medical fluid to a patient already receiving a relatively large amount of a first medical fluid via IV infusion. Rather than administer the second medical fluid through a separate direct injection, the second medical fluid can be injected into the flow of the first medical fluid. A syringe, or other fluid container having an IV line and a luer connector, can be used to actuate a needleless access port in an IV set that connects the container of the first medical fluid to the patient and inject the second medical fluid through the access port. IV sets are commonly provided with one or more needleless access ports for this and other uses.

Needleless access ports typically have internal spaces surrounding the self-sealing elements of the access port. These internal spaces are typically connected through a single opening to the primary line of the IV set such that the flow through the internal space is to or from the needleless connector that is actuating the access port. When the IV set is initially set up, this space may not be flushed with fluid introduced into the primary line, leaving this space filled with air. This requires manual flushing of the access port, either by introduction of fluid into the access port to force this air into the primary line where it is carried away and expelled during the set-up or connection of an empty syringe and extraction of the air through the access port.

When a second medical fluid is injected through the needleless access port, a certain amount of the injected second medical fluid remains in the interior space and does not reach the patient. To administer the entire prescribed dose of the second medical fluid to the patient, the caregiver must connect a second syringe, or other fluid container having a Luer fitting, containing a flushing fluid, for example saline, and inject a sufficient quantity of this flushing fluid to flush the interior space and carry the second medical fluid into the main line of the IV set. This creates an additional work step for the caregiver and adds a risk to the patient of infection due to the additional manipulation of the device.

Alternately, a caregiver may administer an extra amount of the second medical fluid such that the prescribed dose reaches the main line of the IV set. This creates a risk that a second caregiver, not realizing that there is residual second medical fluid in the access port, may also administer an extra amount of the second medical fluid and thereby administer more than the intended amount.

SUMMARY

It is desirable to provide an infusion set with a needleless access port without a trapped internal space such that all air in the IV set is displaced by liquid during the initial set-up and the entire volume of medical fluid introduced into the access port reaches the patient without the need for manually flushing the access port. Within this disclosure, the phrase "needleless" is used interchangeably with the phrase "luer" and "Luer," as a Luer fitting is an exemplary and common embodiment of a needleless connection system. Likewise, the phrases "connector" and "fitting" are used interchangeably to refer to either of the male or female elements of a needleless connector.

The present disclosure includes systems and methods adapted to cause the fluid moving through the primary line to flush the internal space of the attached needleless access port.

In certain embodiments, a valve is provided that comprises a body having an inlet and an outlet, and a needleless access port coupled to the body. The access port is configured to be actuated by a Luer fitting. The access port comprises an interior space. The inlet is selectively coupled to the outlet through the interior space such that fluid entering the inlet entirely flows through the interior space to the outlet.

In certain embodiments, a IV set is provided that comprises a valve that comprises a body having an inlet and an outlet, and a needleless access port coupled to the body. The access port is configured to be actuated by a Luer fitting. The access port comprises an interior space. The inlet is selectively coupled to the outlet through the interior space such that fluid entering the inlet entirely flows through the interior space to the outlet. The IV set also comprises at least one fluid line fluidically coupled to one of the inlet and outlet of the valve.

In certain embodiments, a IV set is provided that comprises a needleless access port comprising an interior space, and first and second fluid lines fluidically coupled to the access port such that all fluid flowing through the first fluid line passes into the interior space of the access port and then into the second line.

In certain embodiments, a valve is provided that comprises a body having a first port, a second port, and a third port. The third port comprises a self-sealing access port configured to be actuated by a Luer fitting. Fluid expelled from the luer connector when actuating the access port is deposited directly into an internal fluid space. Fluid entering the first port entirely flows through the interior space to the second port.

In certain embodiments, a method of intravenously administering a medication to a patient is provided. The method comprising the step of allowing a medical fluid to flow from a container to a Luer fitting that is fluidically coupled to the patient through a valve that is coupled between the container and the infusion device. The valve comprises a body and a needleless access port coupled to the body. The body has an inlet and an outlet and the access port is configured to be actuated by a Luer fitting. The access port comprises an interior space. The inlet is selectively coupled to the outlet through the interior space such that the medical fluid flows from the container entirely through the interior space to the patient. The method also comprises the steps of actuating the access port by connecting a luer connector that is coupled to a source of the medication, and allowing the medication to flow from the source into the interior space of the access port.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The following description discloses embodiments of systems and methods for introducing a second fluid into a primary line carrying a first fluid through a needleless access port without requiring flushing of the access port to remove air or flush a trapped volume of the second fluid into the primary line.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. The systems and methods disclosed herein are discussed in the context of an IV set that includes a valve and a needleless access port being used to administer medical fluids to a patient in a healthcare environment. Nothing herein should be interpreted to limit the coverage of the claims to a healthcare environment or to IV sets unless specifically stated as such.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

Figure 1A:
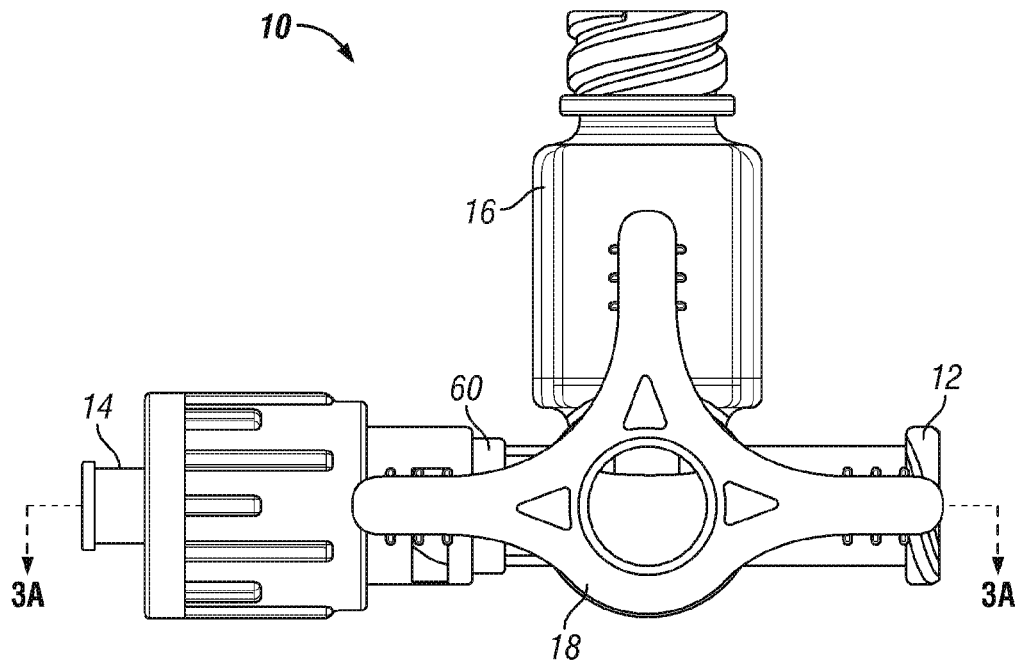
FIGS. 1A and 1B are an external view and a cross-section, respectively, of an exemplary device in a first configuration according to certain aspects of the present disclosure.
Figure 1B:
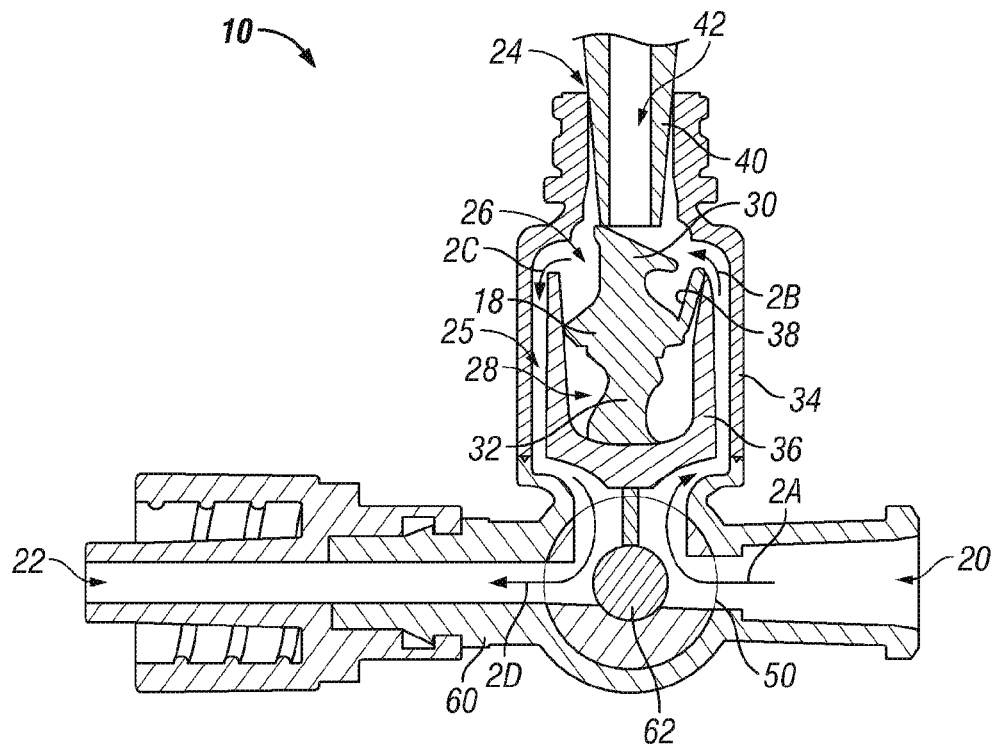

FIGS. 1A and 1B are an external view and a cross-section, respectively, of an exemplary device 10 in a first configuration according to certain aspects of the present disclosure. As shown in FIG. 1A, the device 10 has a body 60 with an outlet connector 14, configured in the depicted embodiment as a male quick-connect fitting, and an inlet connector 12, configured in the depicted embodiment as a female Luer fitting. The device 10 also has a needleless access port 16 coupled to the body 60 and a rotatable element 50 (not visible in FIG. 1A) disposed partially within the body 60. An external handle 18 is coupled to the rotatable element 50. The exemplary handle 18 of FIG. 1A is configured with three lobes that correspond, in the various positions described herein, to the ports that are coupled together when the handle is in a particular position. For example, in the configuration of FIGS. 1A and 1B, all three ports 12, 14, and 16 are connected.

FIG. 1B depicts the flow paths within the device 10 with the handle 18, and therefore the rotatable element 50, in a first configuration or position. The rotatable element 50 has four ports that are described in greater detail with respect to FIG. 1C. The body comprises a post 62 that protrudes into the center of the rotatable element 50. The rotatable element 50 moves along its axis of rotation when it rotates. In the configuration of FIG. 1B, the rotatable element 50 is positioned such that the post 62 completely blocks the channel 58A (identified in FIG. 2B) through the rotatable element 50, forcing the liquid that enters the inlet 20 of inlet connector 12 to follow the arrow 2A and flow into the access port 16. The liquid flows through a channel 25 in the access port 16 and follows arrow 2B into an interior space 26 that surrounds the valve plug 18, then follows arrow 2C into a second channel 25 that guides the fluid back to the rotatable element 50 where the fluid flows as indicate by arrow 2D to the outlet 22 of the connector 14.

The valve plug 18 has an upper portion 30, a lower portion 32, and a membrane 38 that is sealed to the access port body 36 of the access port 16. The membrane 38 seals off a portion 28 of the interior space 26. In certain embodiments, the portion 28 is vented to the external environment through an air channel (not shown) through the access port body 36. When the access port 16 is not actuated, the upper portion 30 is positioned such that a surface of the upper portion 30 is flush with the entrance 24 of the access port 16. When device 10 is not actuated, fluid continues to flow through the interior space 26 following the path indicated by arrows 2A, 2B, 2C, and 2D. When an IV set that includes a device 10 is first set up, the flow of medical fluid through the device 10 will flush the air that is initially within the interior space 26 out through the outlet 22, eliminating the need to manually flush the access port 16.

When the access port 16 is actuated, as shown in FIG. 1B, by a luer connector 40, the upper portion 30 is displaced downward into the interior space 26. This displacement compresses the lower portion 32 against an inner surface of the access port body 36 and also stretches the membrane 38, creating restorative forces that will urge the upper portion 30 back to the original position when the luer connector 40 is removed, thereby sealing the access port 16.

The interior space 26 is fluidically coupled to a lumen 42 within the luer connector 40 such that fluids, such as a medical fluid or medication, may be introduced into the interior space 26 through the luer connector 40 or fluids may be extracted from the interior space 26 through the luer connector 40. As previously discussed, a first medical fluid entering the device 10 through inlet 20 will pass through the interior space 26 and then to the outlet 22 when the device 10 is in the configuration of FIG. 1B. A second medical fluid introduced through entrance 24 of the access port 16 will mix with the first medical fluid in the interior space 26 and be carried with the first medical fluid to the outlet 22. When the introduction of the second medical fluid is complete, and the luer connector 40 withdrawn, any residue of the second medical fluid in the interior space 26 will be flushed by the first medical fluid flowing through the interior space 26, thereby ensuring that the entire dose of the second medical fluid that was injected into the entrance 24 reaches the patient. This eliminates the need to manually flush the access port 16 with a flushing liquid to cause the entire administered dose of the second medical fluid to reach the patient. This also reduces the risk of an overdose of the second medical fluid as there is no residual pocket of the second medical fluid that may create an overdose in a subsequent administration of a medical fluid through the access port 16.

The interior space 26 is fluidically isolated from the portion 28 such that fluid in the interior space 26 cannot enter the portion 28. The portion 28 has a first volume when the device 10 is not actuated and a second volume when the device 10 is actuated by a luer connector 40. The fluid-filled interior space 26 has a first volume when the device 10 is not actuated and a second volume when the device 10 is actuated by a luer connector 40. In certain embodiments, the second volume of interior space 26 is large than the first volume of the interior space 26, while the second volume of the portion 28 is smaller than the first volume of the portion 28. This creates a positive displacement of fluid from the interior space 26 as the luer connector 40 is withdrawn from the access port 16. In certain embodiments, the access port 16 is configured such that the first volume of the interior space 26 is larger than the second volume of the interior space 26, thereby creating a negative displacement, i.e. drawing fluid into the interior space 26 as the luer connector 40 is withdrawn from the access port 16. This may be beneficial to reduce the exposure of the caregiver and patient to the pure second medical fluid, as medical fluid that might leak out through entrance 24 will be sucked into the interior space 26 as the luer connector 40 is withdrawn from the entrance 24.

Figure 1C:
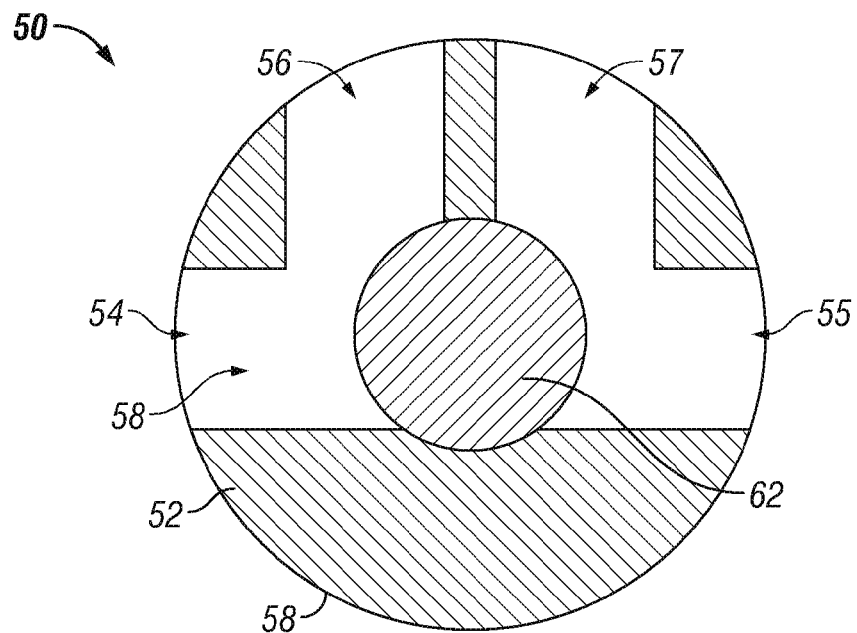
FIG. 1C is an enlarged cross-section of the rotatable element of FIG. 1B according to certain aspects of the present disclosure.

FIG. 1C is an enlarged cross-section of the rotatable element of FIG. 1B according to certain aspects of the present disclosure. The rotatable element 50 has four ports 54, 55, 56, 57 located on a cylindrical external surface 58 and a central bore on the axis of rotation of the rotatable element 50 that, in the configuration of FIG. 1B, is filled by post 62 of the body 60. As previously discussed, the post 62 blocks the channel 58A that directly connects port 54 to port 55 in this configuration of the rotatable element 50 within the device 10, such that port 54 is fluidically coupled only to side port 56 and side port 57 is fluidically coupled only to port 55. This creates the flow path indicated by arrows 2A, 2B, 2C, and 2D in FIG. 1B.

Figure 1D:
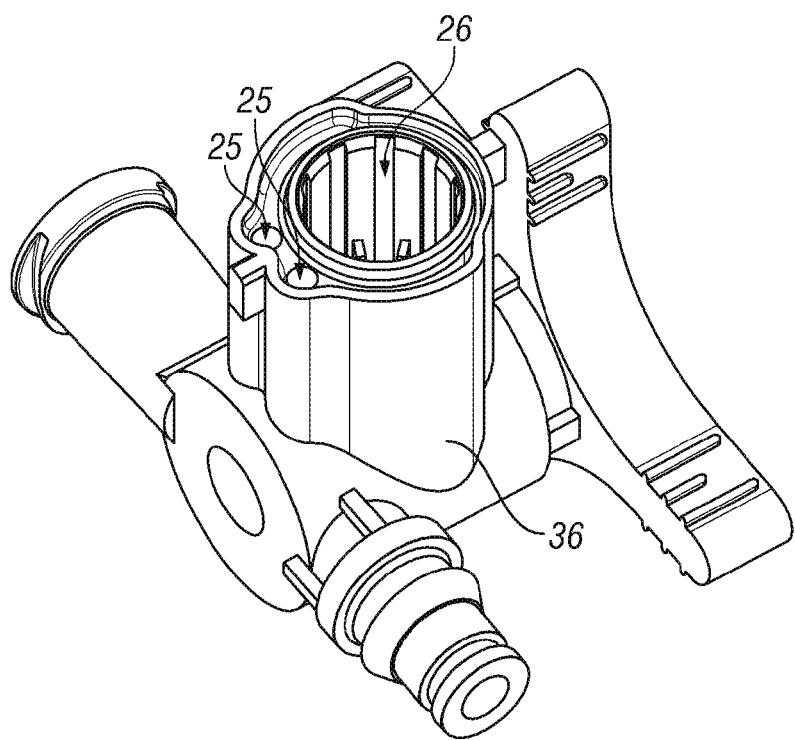
FIG. 1D is a perspective view of an exemplary embodiment of the body of the valve of FIG. 1B according to certain aspects of the present disclosure.

FIG. 1D is a perspective view of an exemplary embodiment of the body 36 of the device 10 of FIG. 1B according to certain aspects of the present disclosure. In this view, the upper portion of the access port 16 and the valve plug 18 have been removed to reveal the interior space 26 and the channels 25 that connect the rotatable element 50 to the interior space 26.

Figure 2A:
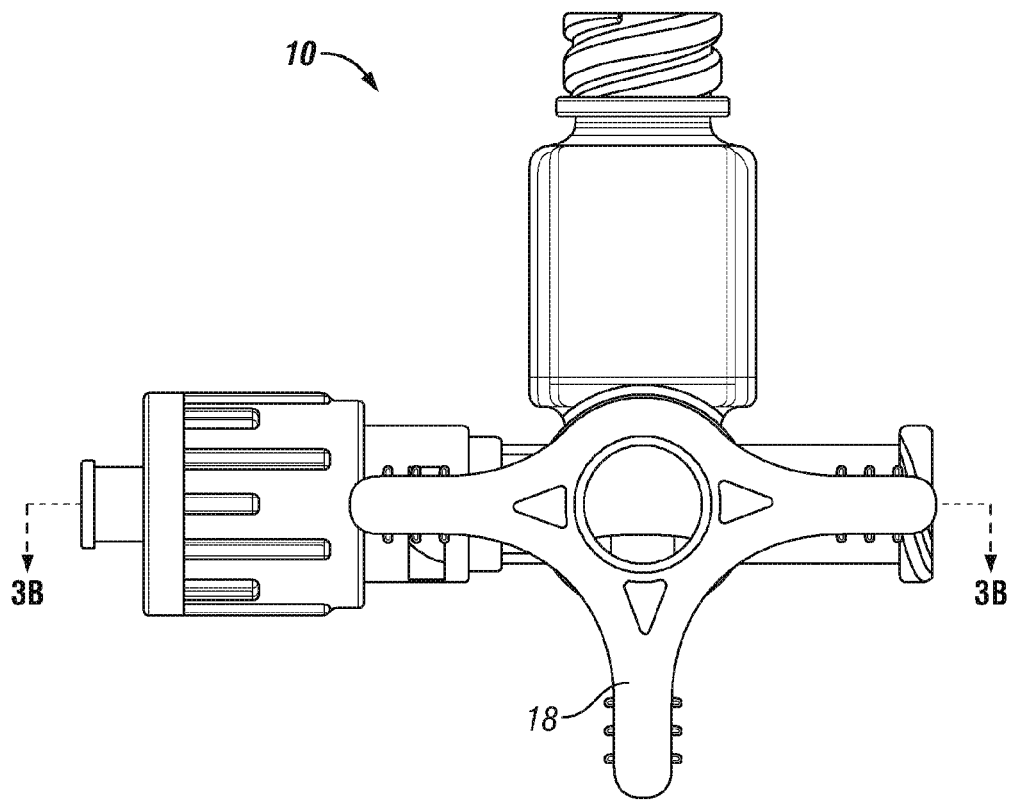
FIGS. 2A and 2B are an external view and a cross-section, respectively, of the valve of FIGS. 1A and 1B in a second configuration according to certain aspects of the present disclosure.
Figure 2B:
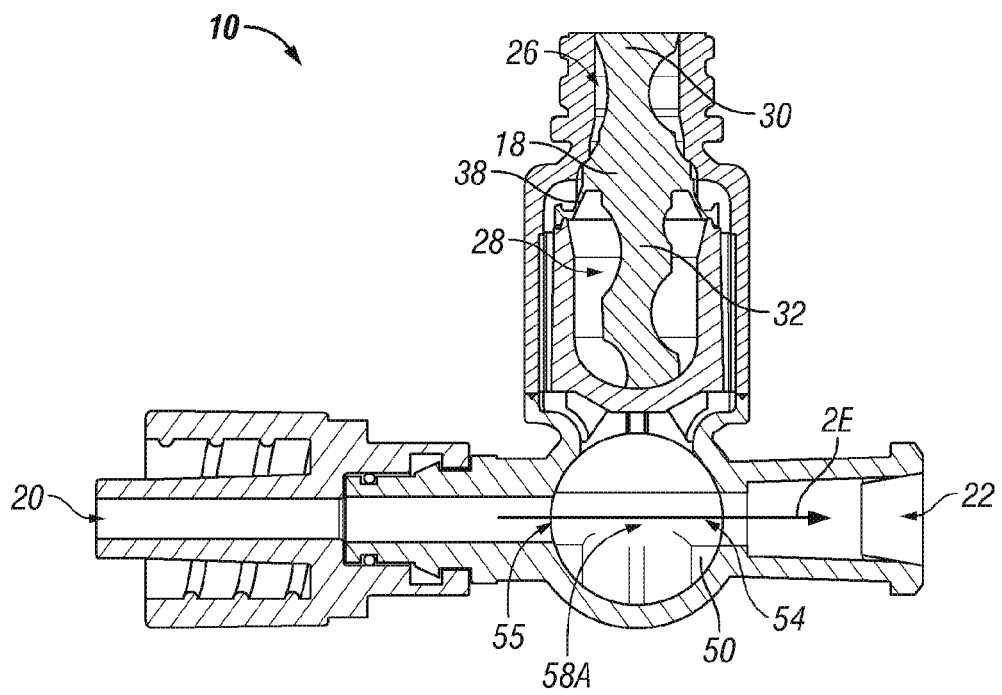

FIGS. 2A and 2B are an external view and a cross-section, respectively, of the device 10 of FIGS. 1A and 1B in a second configuration according to certain aspects of the present disclosure. It can be seen that the tri-lobed handle 18 in FIG. 2A is rotated 180 degrees with respect to the position of FIG. 1A.

In FIG. 2B, it can be seen that the rotatable element 50 is also 180 degrees with respect to the position of the rotatable element 50 in FIG. 1B. In this configuration, the rotatable element 50 is also displaced with respect to the body 60 along the axis of rotation, moving out of the page in the view of FIG. 2B, such that post 62 no longer blocks the channel 58A in the rotatable element 50 that directly connects ports 54 and 55. The other ports 56, 57 are blocked in this configuration, such that all fluid that flows into inlet 20 flows into port 55 through channel 58A directly to port 54 as indicated by arrow 2E and on to the outlet 22. The access port 16 is isolated from the fluid flow path in this configuration.

Figure 3A:
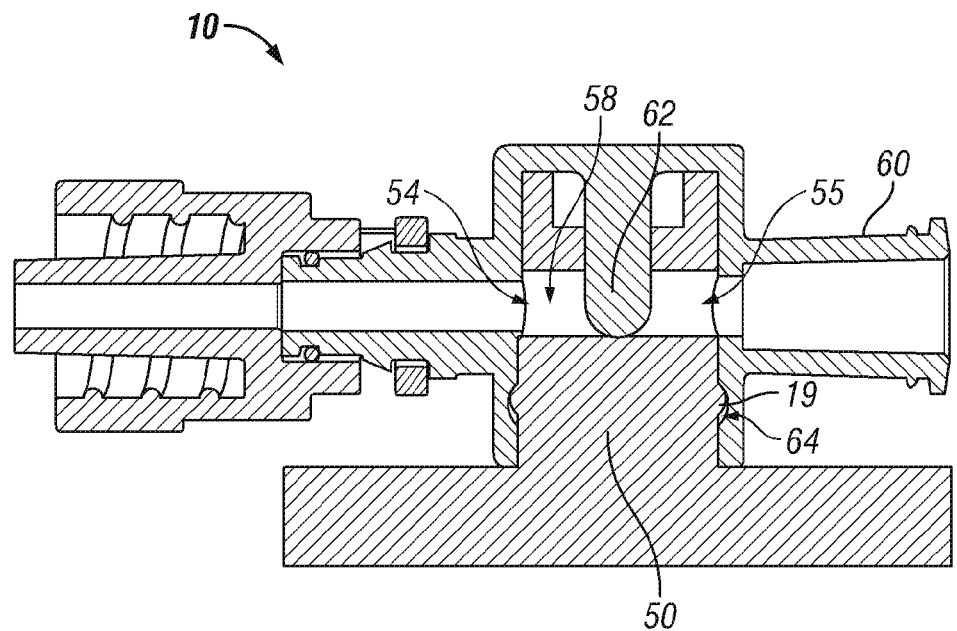
FIG. 3A is a cross-section of the valve of FIGS. 1A and 1B in the first configuration according to certain aspects of the present disclosure.

FIG. 3A is a cross-section of the device 10 of FIGS. 1A and 1B in the first configuration according to certain aspects of the present disclosure. It can be seen that the rotatable element 50 comprises a travel stop 19 that, in this embodiment, is a ridge passing around a circumference of the rotatable element 50. The travel stop 19 is disposed within a recess 64 in the body 60. When the rotatable element 50 is forced upwards, in the view of FIG. 3A, by a shaped portion (not shown) of the rotatable element 50, then the post 62 contacts the lower side of the channel 58 before the travel stop reaches the side of recess 64. This blocks flow through the channel 58 from port 54 to port 55, as discussed with respect to FIG. 1B.

Figure 3B:
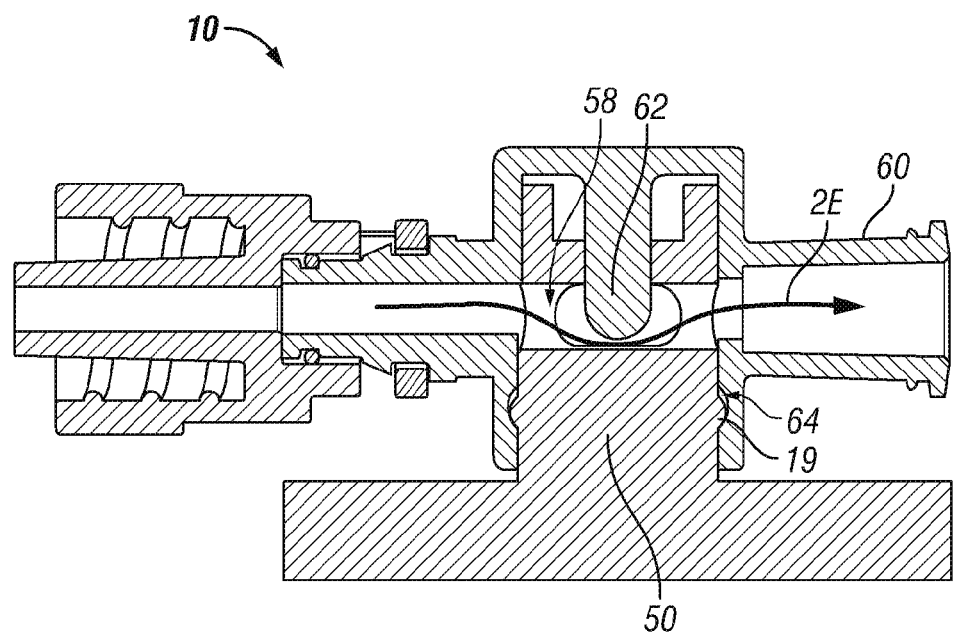
FIG. 3B is a cross-section of the valve of FIGS. 1A and 1B in the second configuration according to certain aspects of the present disclosure.

FIG. 3B is a cross-section of the device 10 of FIGS. 1A and 1B in the second configuration according to certain aspects of the present disclosure. It can be seen that the rotatable element 50 has been displaced downward by the shaped portion (not shown) until the travel stop 19 contacts the lower edge of the recess 64, thereby opening a gap between the post 62 and the side of channel 58. This allows direct flow between ports 55 and 54.

Figure 4A:
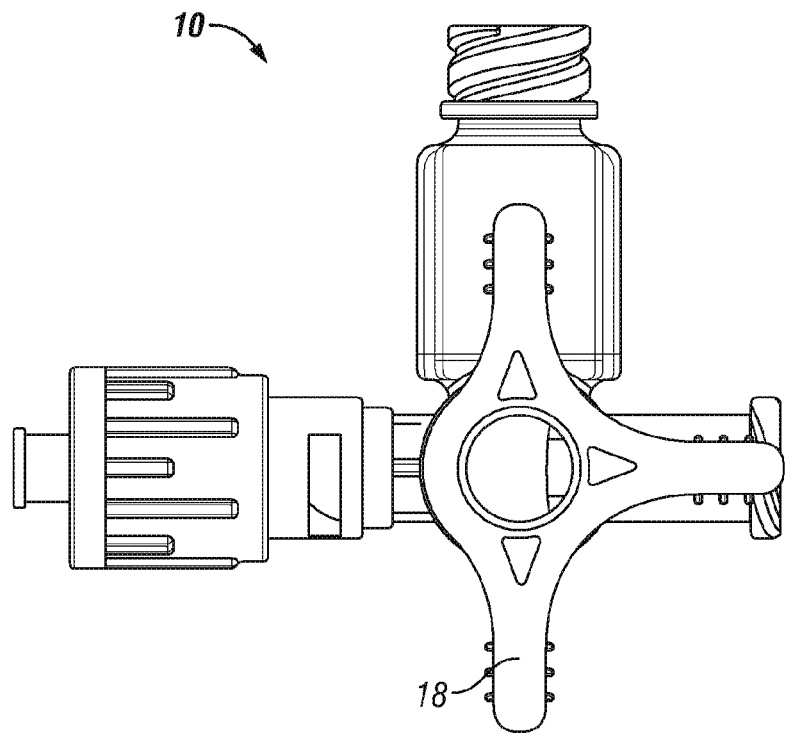
FIGS. 4A and 4B are an external view and a cross-section, respectively, of the valve of FIGS. 1A and 1B in a third configuration according to certain aspects of the present disclosure.
Figure 4B:
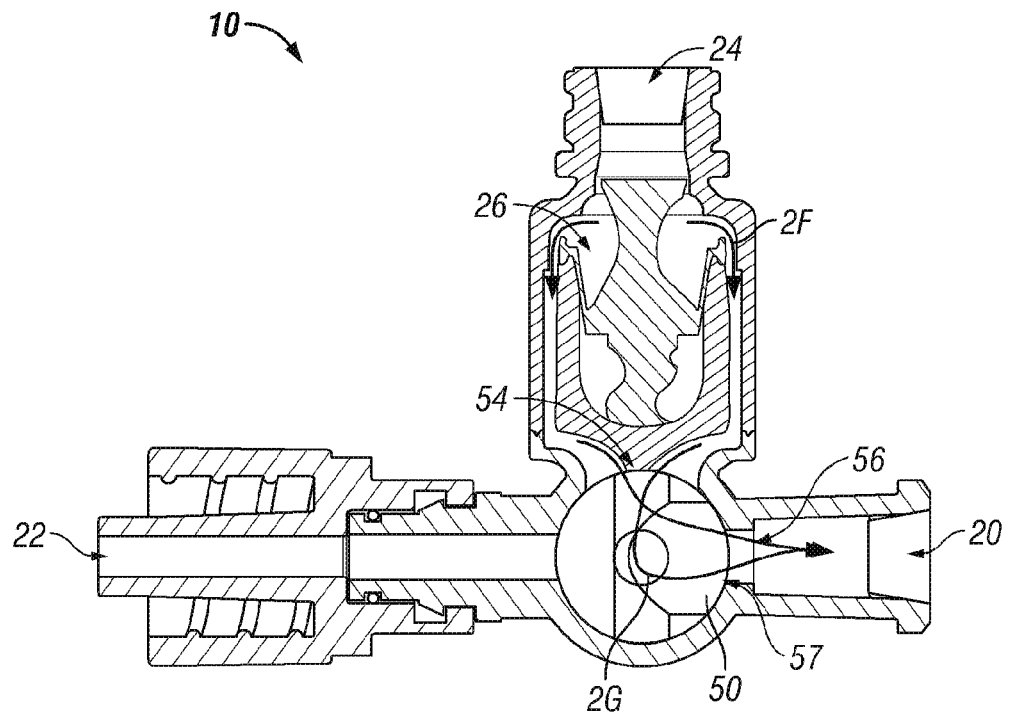

FIGS. 4A and 4B are an external view and a cross-section, respectively, of the device 10 of FIGS. 1A and 1B in a third configuration according to certain aspects of the present disclosure. In the position of the handle 18 shown in FIG. 4A, it can be seen in FIG. 4B that the port 54 is fluidically coupled to both channels 25 in the access port 16 and that both ports 56 and 57 are fluidically coupled to the inlet 20. This configuration is advantageous for injecting a medical fluid through entrance 24 of the access port 16 and guiding the injected medical fluid as indicated by the arrows 2F and 2G solely to the inlet 20, while preventing any of the fluid from passing out the outlet 22.

Figure 5A:
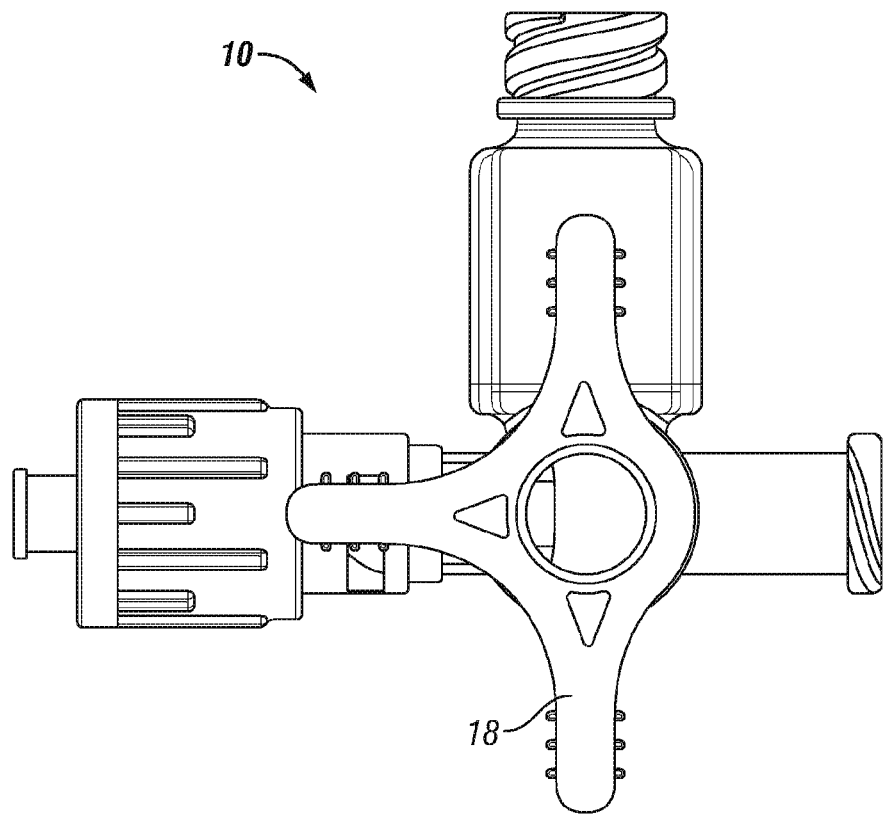
FIGS. 5A and 5B are an external view and a cross-section, respectively, of the valve of FIGS. 1A and 1B in a fourth configuration according to certain aspects of the present disclosure.
Figure 5B:
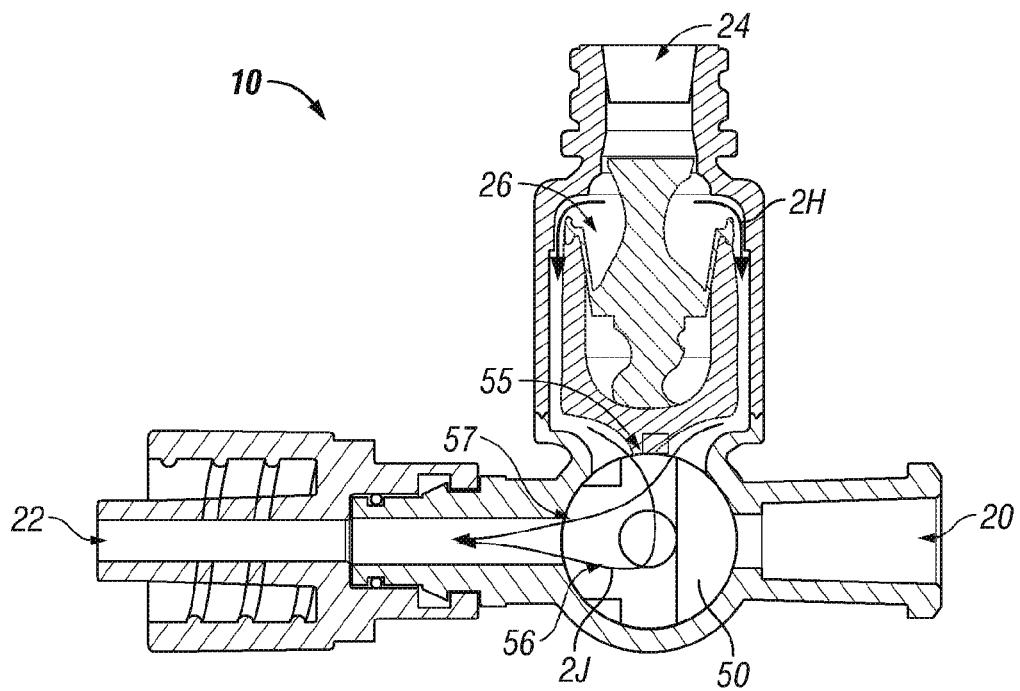

FIGS. 5A and 5B are an external view and a cross-section, respectively, of the valve of FIGS. 1A and 1B in a fourth configuration according to certain aspects of the present disclosure. In the position of the handle 18 shown in FIG. 4A, it can be seen that the flow paths are reversed from those shown in FIG. 4B. Port 55 is now coupled to both of the channels 25 of the access port 16, and the ports 56, 57 are both coupled to the outlet 22. This configuration is advantageous for injecting a medical fluid through entrance 24 of the access port 16 and guiding the injected medical fluid as indicated by the arrows 2H and 2J solely to the outlet 22, while preventing any of the fluid from passing out the inlet 20.

Figure 6:
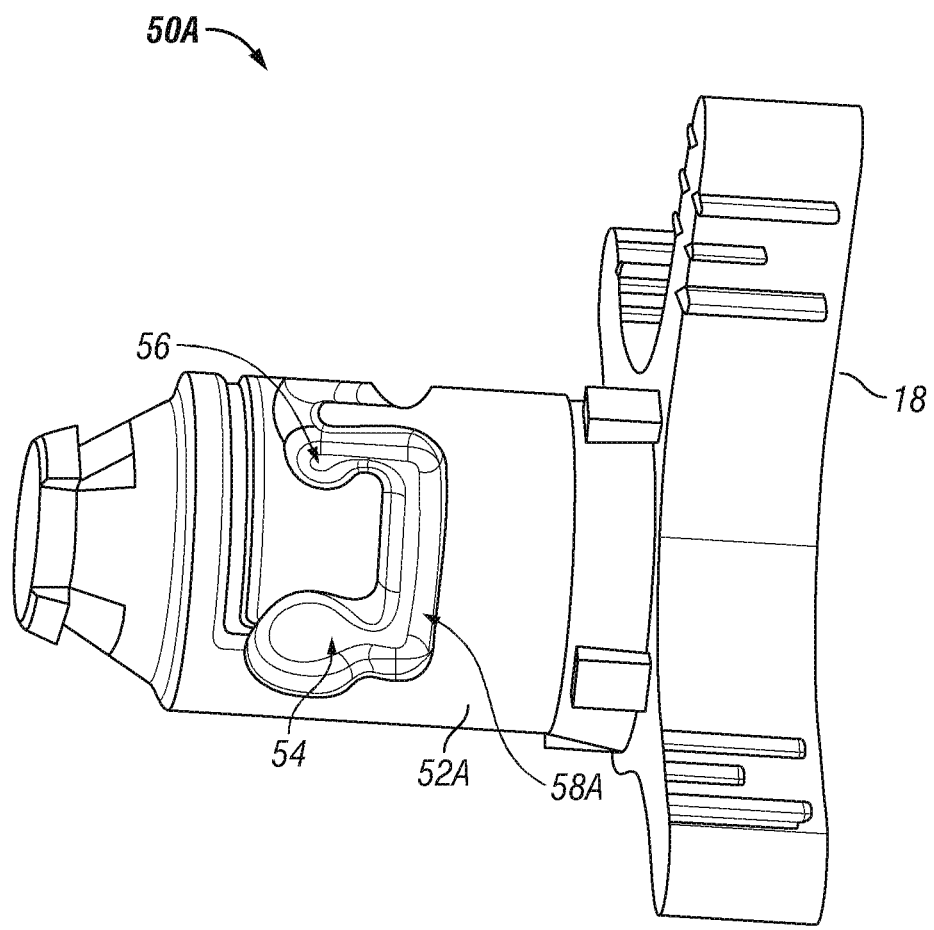
FIG. 6 is another embodiment of the rotatable element according to certain aspects of the present disclosure.

FIG. 6 is another embodiment of the rotatable element 50A according to certain aspects of the present disclosure. In this embodiment, the fluid passages between the ports are formed as recessed channels 58A in an outer surface of the body 52A, instead of passages 58A passing through the body 52 as seen in FIG. 1C. The channel 58A connecting port 54 to port 56 is visible in FIG. 6.

The disclosed self-flushing valve is configured to direct a first medical fluid flowing from the inlet to the outlet of the valve through the interior space of the access port, thereby automatically flushing this interior volume. The disclosed valve is advantageous in that the interior space of the access port is flushed of air during set-up by the first medical fluid flowing through the valve without the need for manually injecting fluid or extracting air through the access port, thereby reducing the workload of the caregiver and reducing the risk that residual air may be passed through the connected IV lines to the patient. Similarly, the total volume of a second medical fluid injected into the access port is flushed by the first medical fluid passing through the valve without the need to manually inject a flushing liquid into the access port or inject an extra amount of the second medical fluid to force the prescribed amount into the main channel. This again reduces the workload of the caregiver while also reducing the risk of an overdose when residual second medical fluid remains trapped in a non-flushed volume of the access port.

It is understood that the specific order or hierarchy of steps or blocks in the processes disclosed is an illustration of exemplary approaches. Based upon design preferences, it is understood that the specific order or hierarchy of steps or blocks in the processes may be rearranged. The accompanying method claims present elements of the various steps in a sample order, and are not meant to be limited to the specific order or hierarchy presented.

It is understood that the designation of inlet and outlet are arbitrary and that fluid may enter the connector through the port identified as the outlet and flow through the connector and out through the port identified as the inlet.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims.

Reference to an element in the singular is not intended to mean "one and only one" unless specifically so stated, but rather "one or more." Unless specifically stated otherwise, the term "some" refers to one or more.

Pronouns in the masculine (e.g., his) include the feminine and neuter gender (e.g., her and its) and vice versa. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "operation for."

Although embodiments of the present disclosure have been described and illustrated in detail, it is to be clearly understood that the same is by way of illustration and example only and is not to be taken by way of limitation, the scope of the present invention being limited only by the terms of the appended claims.

What is claimed is:

1. A valve comprising:
   a body having a first port, a second port, a third port, and a post, wherein the third port comprises a self-sealing access port configured to be actuated by a Luer fitting, wherein fluid expelled from the Luer fitting when actuating the access port is deposited directly into an internal fluid space;
   a rotatable element having an inlet port, an outlet port, first and second side ports, a direct passage from the inlet port directly to the outlet port, and an axis of rotation, the rotatable element disposed within the body so that the post protrudes into the direct passage;
   the body and rotatable element are configured to cooperatively displace the rotatable element with respect to the body along the axis of rotation as the rotatable element is moved between a first and a second configuration;
   wherein the post blocks the direct passage when the rotatable element is in the first configuration so that fluid entering the first port entirely flows through the internal fluid space to the second port.

2. An intravenous (IV) set comprising:
   a valve comprising:
      a body having an inlet, an outlet, and a post;
      a needleless access port coupled to the body, the access port configured to be actuated by a needleless connector, the access port comprising an interior space; wherein the inlet is selectively coupled to the outlet through the interior space such that fluid entering the inlet entirely flows through the interior space to the outlet;
      a rotatable element having an inlet port, an outlet port, first and second side ports, a direct passage from the inlet port directly to the outlet port, and an axis of rotation, the rotatable element disposed within the body so that the post protrudes into the direct passage;
      the body and rotatable element are configured to cooperatively displace the rotatable element with respect to the body along the axis of rotation as the rotatable element is moved between a first and a second configuration, the post blocks the direct passage when the rotatable element is in the first configuration; and the direct passage is at least partially open when the rotatable element is in the second configuration; and
   at least one fluid line fluidically coupled to one of the inlet and outlet of the valve.

3. The IV set of claim 2, wherein:
   the needleless connector comprises a lumen; and
   the lumen is fluidically coupled to the interior space while the connector is actuating the access port.

4. The IV set of claim 3, wherein, in the first configuration, the inlet is coupled to the outlet through the interior space.

5. The IV set of claim 4, wherein:
   the rotatable element and the body are configured such that the inlet port is fluidically coupled only to the first side port and the outlet port is fluidically coupled only to the second side port when the rotatable element is in the first configuration.

6. The IV set of claim 4, wherein, in the second configuration, the inlet is fluidically coupled directly to the outlet such that at least a portion of fluid entering the inlet flows to the outlet without passing through the interior space.

7. The IV set of claim 6, wherein the access port is fluidically isolated from the inlet and the outlet when the rotatable element is in the second configuration.

8. An IV set comprising:
   a valve comprising:
      a body having an inlet, an outlet, and a post;
      a needleless access port coupled to the body, the access port configured to be actuated by a needleless connector, the access port comprising (i) an interior space and (ii) a portion fluidically isolated from the interior space, the portion remaining fluidically isolated from the interior space when the access port is not actuated and when actuated, wherein the inlet is selectively coupled to the outlet through the interior space such that fluid entering the inlet entirely flows through the interior space to the outlet; and
      a rotatable element having an inlet port, an outlet port, first and second side ports, a direct passage from the inlet port directly to the outlet port, and an axis of rotation, the rotatable element disposed within the body so that the post protrudes into the direct passage;

the body and rotatable element are configured to cooperatively displace the rotatable element with respect to the body along the axis of rotation as the rotatable element is moved between a first and a second configuration, the post blocks the direct passage when the rotatable element is in the first configuration; and the direct passage is at least partially open when the rotatable element is in the second configuration; and first and second fluid lines fluidically coupled to the access port such that all fluid flowing through the first fluid line passes into the interior space of the access port and then into the second line.

9. A valve comprising:

a body having an inlet, an outlet, and a post;

a needleless access port coupled to the body, the access port configured to be actuated by a needleless connector, the access port comprising an interior space; wherein the inlet is selectively coupled to the outlet through the interior space such that fluid entering the inlet entirely flows through the interior space to the outlet; and a rotatable element having an inlet port, an outlet port, first and second side ports, a direct passage from the inlet port directly to the outlet port, and an axis of rotation, the rotatable element disposed within the body so that the post protrudes into the direct passage;

the body and rotatable element are configured to cooperatively displace the rotatable element with respect to the body along the axis of rotation as the rotatable element is moved between a first and a second configuration, the post blocks the direct passage when the rotatable element is in the first configuration; and the direct passage is at least partially open when the rotatable element is in the second configuration.

10. The valve of claim 9, wherein:

the needleless connector comprises a lumen; and the lumen is fluidically coupled to the interior space while the needleless connector is actuating the access port.

11. The valve of claim 9, wherein, in the first configuration, the inlet is coupled to the outlet through the interior space.

12. The valve of claim 11, wherein the rotatable element and the body are configured such that the inlet of the body is fluidically coupled to the inlet port that is fluidically coupled only to the first side port and the outlet of the body is fluidically coupled to the outlet port that is fluidically coupled only to the second side port and the first and second side ports are separately coupled to the interior space of the access port when the rotatable element is in the first configuration.

13. The valve of claim 11, wherein, in the second configuration, the inlet is fluidically coupled directly to the outlet such that at least a portion of fluid entering the inlet flows to the outlet without passing through the interior space.

14. The valve of claim 13, wherein the access port is fluidically isolated from the inlet and the outlet when the rotatable element is in the second configuration.

15. The valve of claim 9, wherein:

the access port further comprises a portion fluidically isolated from the interior space; the portion has a first volume when the access port is not actuated and a second volume when actuated; and the first volume is greater than the second volume.

* * * * *